(12) United States Patent
Kautz et al.

(10) Patent No.: US 7,687,269 B2
(45) Date of Patent: Mar. 30, 2010

(54) METHOD FOR EFFICIENT TRANSPORT OF SMALL LIQUID VOLUMES TO, FROM OR WITHIN MICROFLUIDIC DEVICES

(75) Inventors: Roger A. Kautz, Nahant, MA (US); Barry L. Karger, Newton, MA (US)

(73) Assignee: Northeastern University, Boston, MA (US)

( * ) Notice: Subject to any disclaimer, the term of this patent is extended or adjusted under 35 U.S.C. 154(b) by 823 days.

(21) Appl. No.: 10/582,599

(22) PCT Filed: Dec. 10, 2004

(86) PCT No.: PCT/US2004/041923

§ 371 (c)(1), (2), (4) Date: Jun. 9, 2006

(87) PCT Pub. No.: WO2005/059512

PCT Pub. Date: Jun. 30, 2005

(65) Prior Publication Data

US 2007/0117212 A1    May 24, 2007

Related U.S. Application Data

(60) Provisional application No. 60/528,410, filed on Dec. 10, 2003.

(51) Int. Cl.
*G01N 35/08* (2006.01)
(52) U.S. Cl. .................. 436/52; 436/173; 436/174; 436/180; 422/100; 422/68.1; 548/100
(58) Field of Classification Search ............. 435/287.2, 435/286.5; 422/64, 82.08
See application file for complete search history.

(56) References Cited

U.S. PATENT DOCUMENTS

| | | | |
|---|---|---|---|
| 3,479,141 A | 11/1969 | Smythe et al. | |
| 6,130,098 A | 10/2000 | Handique et al. | ........... 436/180 |
| 6,372,353 B2 | 4/2002 | Karger et al. | |
| 6,508,988 B1 | 1/2003 | Van Dam et al. | ............ 422/102 |
| 6,524,456 B1 | 2/2003 | Ramsey et al. | |
| 6,645,432 B1 * | 11/2003 | Anderson et al. | ........... 422/100 |
| 6,706,519 B1 * | 3/2004 | Kellogg et al. | ........... 435/287.2 |
| 6,808,745 B2 * | 10/2004 | Yang | ....................... 427/248.1 |
| 7,032,607 B2 | 4/2006 | Burns | |
| 7,129,091 B2 | 10/2006 | Ismagilov et al. | |
| 2002/0187074 A1 | 12/2002 | O'Connor et al. | ........ 422/82.05 |

(Continued)

OTHER PUBLICATIONS

Behnia et al. Anal. Chem. 1998, 70, pp. 5326-5331.*

(Continued)

*Primary Examiner*—Jill Warden
*Assistant Examiner*—Sally A Sakelaris
(74) *Attorney, Agent, or Firm*—Weingarten, Schurgin, Gagnebin & Lebovici LLP

(57) ABSTRACT

Methods are presented for realizing zero-dispersion segmented flow for transfer of small microfluidic samples onto or within microfluidic analysis or processing devices. Where fluidic systems are in whole or in part made of materials favorable to the zero-dispersion conditions for an indicated solvent/carrier fluid system, the system may be covalently coated to impart the necessary surface properties. This invention is demonstrated in an embodiment where 1 microliter samples (6) are robotically prepared and transferred through 3 meters of capillary tubing (4) to a microcoil NMR probe.

20 Claims, 9 Drawing Sheets

U.S. PATENT DOCUMENTS

| | | | |
|---|---|---|---|
| 2003/0006140 A1 | 1/2003 | Vacca et al. | 204/547 |
| 2003/0124736 A1 | 7/2003 | Manz et al. | 436/180 |
| 2003/0232450 A1 | 12/2003 | Yoshida | 436/180 |
| 2004/0052929 A1 | 3/2004 | Kirby et al. | |
| 2006/0108012 A1 | 5/2006 | Barrow et al. | |

OTHER PUBLICATIONS

Adler, H. et al., "Continuous Extraction of Body Fluid Samples, Including Whole Blood, Plasma and Urine"; Advances in Automated Analysis, Technicon International Congress, vol. IX; Mediad Inc., Tarrytown, NY; (1973), pp. 81-85.

Behnia, B. and Webb, A.G.; "Limited-Sample NMR Using Solenoidal Microcoils, Perfluorocarbon Plugs, and Capillary Spinning"; Analytical Chemistry; (1998); 70(24): 5326-5331.

Curcio, M and Roeraade, J.; "Continuous Segmented-Flow Polymerase Chain Reaction for High-Throughput Miniaturized DNA Amplification"; Anal. Chem.; (2003) 75: 1-7.

Eldridge, G. R, et al.; "High-Throughput Method for the . Production and Analysis of Large Natural Product Libraries for Drug Discovery"; Anal. Chem.; (2002), 74: 3963-3971.

Kautz, R. A., et al.; "Sample Concentration and Separation for Nanoliter-Volume NMR Spectroscopy Using Capillary Isotachophoresis"; J. Am. Chem. Soc.; (2001); 123: 3159-3160.

Keifer, P.A., "Flow NMR Applications in Combinatorial Chemistry"; Current Opinion in Chemical Biology; (2003a); 7(3): 388-394.

Keifer, P.A., "Flow Injection Analysis NMR (FIA-NMR): A Novel Flow NMR Technique That Complements LC-NMR and Direct Injection NMR (DI-NMR)"; Magnetic Resonance in Chemistry; (2003b); 41(7): 509-516.

Keifer, P.A., et al., "Direct-injection NMR (DI-NMR): A Flow NMR Technique for the Analysis of Combinatorial Chemistry Libraries". J. of Comb. Chem.; (2000); 2(2): 151-171.

Lacey, M.E., et al.; "$^1$H NMR Characterization of the Product from Single Solid-Phase Resin Beads using Capillary NMR Flow Probes"; Journal of Magnetic Resonance; (2001); 153(2): 215-222.

MacNaughtan, M. A., et al., "High-Throughput Nuclear Magnetic Resonance Analysis Using a Multiple Coil Flow Probe"; Anal. Chem.; (2003); 75(19): 5116-5123.

Nord, L. and Karbert, B.; "Extraction Based on the Flow-Injection Principle. Part 6. Film Formation and Dispersion in Liquid-Liquid Segmented Flow Extraction Systems"; Analytica Chimica Acta; (1984);164: 233-249.

Olson D. L. et al.; "Microflow NMR: Concepts and Capabilities"; Analytical Chemistry.; (2004); 76(10) 2966-2974.

Olson, D. L. et al.; "Nanoliter-Volume $^1$H NMR Detection Using Periodic Stopped-Flow Capillary Electrophoresis"; Anal. Chem.; (1999); 71(15): 3070-3076.

Olson, D.L. et al.; "High-Resolution Microcoil $^1$H-NMR for Mass-Limited, Nanoliter-Volume Samples"; Science, (1995);. 270(5244): 1967-70.

Patton, C.J. and A. P. Wade, "Continuous Flow Analyzers"; Analytical Instrumentation Handbook, 2'nd ed. rev., G.W. Ewing, ed., Marcel Dekker, New York; (1997) pp. 152-155 and 207-212.

Song, H., et al.; "A Microfluidic System for Controlling Reaction Networks in Time"; Angew. Chem. Int. Ed.; (2003a); 42(7): 768-772.

Song, H., Ismagilov, R.F.; "Millisecond Kinetics on a Microfluidic Chip Using Nanoliters of Reagents"; J. Am. Chem. Soc.; (2003b); 125(47): 14613-14619.

Webb, A. G., Grant, S.C.; "Signal-to-Noise and Magnetic Susceptibility Trade-offs in Solenoidal Microcoils for NMR"; J. Magn. Reson., Ser. B; (1996); 113: 83-87.

Wolters, A.M., et al., "Microscale NMR"; Anal. Techniques; (2002a); 6: 711-716.

Wolters, A. M et al., "Capillary Isotachophoresis/NMR: Extension to Trace Impurity Analysis and Improved Instrumental Coupling"; Anal. Chem.; (2002b); 74: 2306-2313.

Wolters, A. M., et al.; "NMR Detection with Multiple Solenoidal Microcoils for Continuous-Flow Capillary Electrophoresis"; Anal. Chem.; (2002c); 74: 5550-5555.

Tice, J.D., "Formation of Droplets and Mixing in Multiphase Microfluidics at Low Values of the Reynolds and the Capillary Numbers"; Langmuir; (2003); 19: 9127-9133.

Martin, et al.; "Generation of larger numbers of separated microbial populations by cultivation in segmented-flow microdevices"; Lab Chip; (2003); 3: 202-207.

* cited by examiner

Conventional Flow Injection of uL of dye

Segmented Flow Injection as per the Present Invention

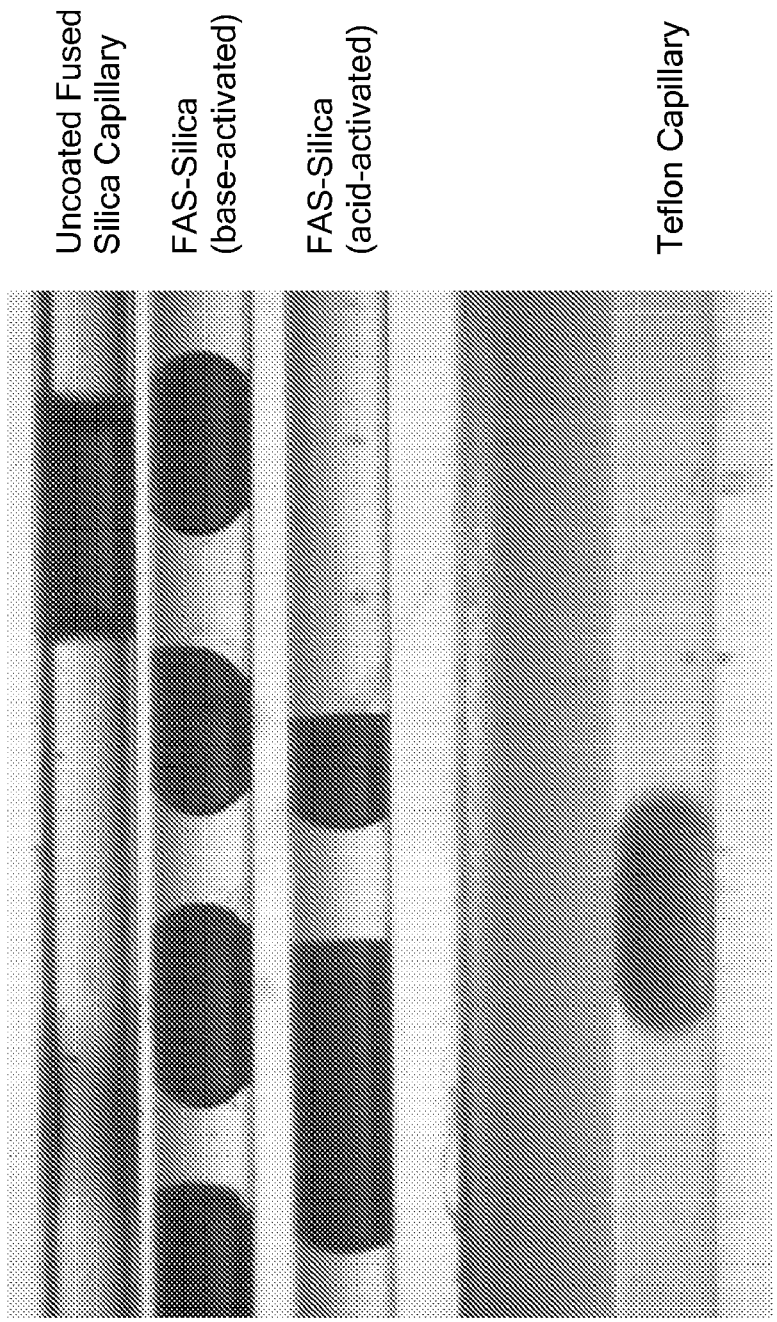
FIG. 2A — Uncoated Fused Silica Capillary
FIG. 2B — FAS-Silica (base-activated)
FIG. 2C — FAS-Silica (acid-activated)
FIG. 2D — Teflon Capillary Sample Recovered After NMR Analysis as per the Present Invention

METHOD FOR EFFICIENT TRANSPORT OF SMALL LIQUID VOLUMES TO, FROM OR WITHIN MICROFLUIDIC DEVICES

CROSS REFERENCE TO RELATED APPLICATIONS

This application claims the priority of U.S. Provisional Application No. 60/528,410 filed Dec. 10, 2003 entitled, METHOD FOR EFFICIENT TRANSPORT OF SMALL LIQUID VOLUMES IN MICROFLUIDIC DEVICES, the whole of which is hereby incorporated by reference herein.

STATEMENT REGARDING FEDERALLY SPONSORED RESEARCH OR DEVELOPMENT

N/A

BACKGROUND OF THE INVENTION

In the last 50 years, and especially in the last decade, there has been a remarkable trend towards both the automation and the miniaturization of chemical analysis and electromechanical systems. The limits of detection of primary analytical methods have improved by many quantum leaps. Mass spectrometry can detect attomoles of sample using nanospray methods. Nuclear Magnetic Resonance (NMR) can now detect pmoles of analyte using 5 nL microcoil probes (Olson, 1995), a 500-fold improvement over 1980's technology. Capillary electrophoresis with laser-induced fluorescence detection (CE-LIF) can detect zeptomoles of analyte in a volume of picoliters. The tremendous sensitivity of these microscale analytical technologies, however, is useless without the ability to efficiently load and deliver the appropriate microscale samples. For example, capillary electrophoresis analysis generally requires providing several microliters of sample, from which a few nanoliters is drawn. Loading a 1 µL microcoil NMR probe requires filling a 10 µL dead volume. On microfluidic chips, samples typically are introduced to fill entire channels, of which only a small segment may occupy a region of detection or be injected into a separation channel.

An obvious alternative would be to supply small samples and drive them through the conduit either with air or with clean solvent. However, in pressure-driven liquid flow, a sample originating as a short volume segment of a conduit will disperse into a larger volume, with concomitant dilution, proportionally to the volume through which it is moved: the boundary layer at the conduit wall is immobile; however, flow at the center of the conduit is rapid. Although dispersion of small concentrated samples can be significant even within the few-cm distances of a microfluidic chip, the problem is most vividly defined and discussed in the example of flow-NMR, where samples must be transported over distances of several meters.

NMR is a very information-rich spectroscopy, well-established for confirming the structure and purity of newly synthesized compounds or isolated natural products. It has also proven valuable in metabonomics, using pattern recognition software to analyze large numbers of complex spectra. However, the low sensitivity of NMR (1000-fold less than mass spectrometry) is problematic, particularly in LC-NMR where acquisition time is limited and compounds of interest may be a small fraction of the permissible column load. NMR sensitivity has been improved modestly (2-4-fold) using higher field magnets and cryogenically-cooled electronics (cryoprobes). For mass-limited samples, microcoil NMR probes offer up to a 500-fold sensitivity increase (Olson, 1995), however, efficiently loading microcoil probes is a challenge (Kautz, 2001). The detection cell has a volume of 30 nL to 1 µL is recessed 50 cm or more up the narrow bore of the NMR magnet. In contrast to conventional NMR probes, the microcoil probe's axis is oriented transverse to the magnet bore so sample tubes cannot be inserted without removing the probe, and consequently microcoil probes are generally implemented as a flow cell. An additional complication is that any motorized equipment must be located outside the magnet's fringe field, necessitating an additional 1-10 meters of capillary tubing, depending on the magnet's fringe field. The current commercial offering is a compromise with these limitations, using the smallest feasible transfer capillaries to fill a relatively large flowcell. But the challenge of filling a 1 µL observed volume in a 5 µL flow cell through several meters of 50 micron capillary tubing (2 µL/meter) has severely limited microcoil NMR's sensitivity in practice.

The two traditional approaches to flow-NMR (Keifer, 2003a) are direct-injection NMR (Keifer, 2000) and flow-injection analysis-NMR (Keifer, 2003b). The methods differ in how they optimize the necessary steps of clearing, washing and reloading the NMR probe flow cell through the 2-5 meter transfer line while avoiding sample dilution in the dead volumes of the transfer line and NMR probe flow cell. In direct injection NMR, samples are injected into an empty (air-filled) flow cell through a 100 µm i.d. or larger transfer line. Samples can be injected relatively quickly without dilution; however, the percentage of the injected sample that ultimately resides within the NMR coil observed volume during spectral analysis, is low. The need for a wash cycle to reduce sample-to-sample carryover to <1% increases the sample change time. Because it is not feasible to flush 50 micron capillaries longer than 1 meter with air, and larger capillaries have a prohibitively large volume, direct injection methods have only been implemented on microcoil probes manually. Working at the closest approach to the magnet bore, it is possible to fill the flow cell using 8 µL samples.

In flow injection NMR, the flow lines are maintained filled with solvent. Samples are introduced by means of a sample loop valve and delivered to the probe by a liquid chromatographic pump. Because the sample disperses into the carrier solvent during transfer, the final analyte concentration in the NMR coil depends on the sample volume, flow rate, and system dead volume. Sharp gradients of analyte concentration near the NMR coil immediately after injection can cause poor line shape, and an equilibration time of 1-2 min may be required for line shape to sharpen as the analyte diffuses throughout the flow cell. Because the effects of these gradients are more pronounced for dissimilar solvents, the same solvent must be used for both the carrier and sample preparation.

FIA-NMR methods are applicable to microcoil probes, and a high-throughput FIA-NMR method using a commercial microcoil probe with a microfluidic sample loader (Olson, 2004) has been introduced. This method requires 10 µL of sample to deliver at full concentration, or dilutes smaller samples to a dead volume of 10 µL in the course of loading. 50 µL of deuterated solvent was also required per sample to reduce carryover below 1%.

Another approach is segmented flow, in which an immiscible fluid is used to push a small sample as a bolus or "plug" through the fluidic conduit. This approach appears to offer several advantages. Smaller samples could be used, so sample consumption would be lower. Samples would not be diluted, so NMR acquisition time would be faster. Samples could be more accurately positioned in the detection cell, so setup would be straightforward, faster and provide better sensitivity. There would be no "equilibration time" required for line-shape to improve after injection. And for high-throughput operation, a queue of samples could be quickly advanced a short distance, rather than having each new sample delivered the entire conduit distance. While the stability of segmented plugs in the 3-mm vertical flow cells of conventional saddle coil LC/NMR probes is problematic, several preliminary findings with segmented plugs in microcoil NMR probes appear promising. Segmented flow has historically been implemented in clinical analyses and has recently been demonstrated in a microfluidic chip (Ramsey, 2003).

In work on the optimal sizes of microcoil probes, it was shown that samples sandwiched on both sides by the immiscible fluorocarbon fluid FC 43 could be much smaller than samples sandwiched between air bubbles without degradation of the NMR line shape: only twice the coil size instead of 7 times (Behnia, 1998). The utility of this fluorocarbon bracketing was demonstrated in obtaining spectra from the 500-ng eluate of a single solid-phase synthesis bead (Lacey, 2001).

However, substantial challenges remain in putting this approach into practice (Macnaughtan, 2003). Sample plugs are frequently lost or degraded in a variety of ways. Principally, moving sample plugs leave a film of solvent on the wall of the conduit, e.g., capillary, and this film can consume about 2 µL of sample per meter of movement, which is completely prohibitive. All of this lost material can mix with subsequent plugs, resulting in high carryover (Patton et al., 1997). Plugs also have tended either to acquire large discrete breaks in the middle ("fragmentation") or to form many small breaks ("frothing") at their ends. Both of these effects increased with increasing capillary size, where the outward pressure of the curved surface of the plug was insufficient to hold the plug against the conduit wall in capillaries over 300 µm diameter. Improvements in these techniques would be greatly appreciated.

BRIEF SUMMARY OF THE INVENTION

The system and method of the invention provide solutions to the problems identified above. This invention is directed to moving small samples through conduits, e.g., the capillary channels or tubing of a microfluidic device, without dilution of the sample or loss of sample to the capillary wall. The transported sample is a small volume of liquid, for example a solution of an analyte for chemical analysis.

In the preferred embodiment of the method of the invention, an aliquot of a liquid that is not miscible with the sample, denominated an "immiscible carrier liquid," is first introduced into a conduit through a microfluidic device. When an aliquot of the sample is subsequently introduced into the conduit, the sample forms a segment or "plug" in the microfluidic channel or capillary, following the carrier liquid. The carrier liquid is pumped or otherwise caused to flow through the channel, and the sample is carried from one location to another through the microfluidic channels without dilution or dispersion into the immiscible carrier liquid. The interior wall of the conduit (channel) is covalently coated with a suitable coating, so that the carrier liquid wets the conduit wall preferentially to the sample solvent. A film of the carrier liquid will then be retained on the channel wall as the sample plug is moved passed, so that the moving sample plug will not contact the conduit wall. This avoids losses of analyte either by binding of analyte molecules to the conduit wall or by bulk loss of sample as a film on the conduit wall.

Preferably, the microfluidic device is part of a conduit system, with attached tubing to transport samples onto and off of the device. Small liquid samples may thus be transported long distances through microfluidic plumbing and through such microdevices with very low losses, and at relatively high speed. As a specific example, if the immiscible carrier liquid is a fluorocarbon (FC), and the channel surface is fluorine-rich, the carrier liquid will wet the channel wall preferentially to both aqueous and organic (hydrophobic and hydrophilic) solvent samples. The desired effect may be obtained either by making a portion of the system, e.g., the attached tubing, of a fluorine-rich material such as a Teflon® (PTFE, ETFE, FEP, NGFP, etc.), or a channel wall, e.g., in the microdevice, may be coated with a fluorine-rich layer such as a fluoroalkyl silane coating on glass, silica, or plastic. In this way, the system and method according to the invention can be used to facilitate the storage of samples for analysis or transport of samples between devices or laboratories. Thus, the present invention improves upon segmented flow as practiced in the prior art by eliminating carryover of aqueous samples on glass or silicon surfaces. Using the method of the invention, it is possible to construct a "chip-to-chip" interface, where two microfluidic devices are interconnected by capillary tubing using the principles of this invention, as an alternative to, for example, having to make a new device with features of the two devices integrated side-by-side to facilitate transferring samples between such devices.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

FIG. 1A shows that 1 µL of dyed DMSO injected in a flowstream of DMSO by the conventional FIA-NMR method has dispersed throughout the flow-cell. FIG. 1B shows that 1 µL of dyed DMSO, when injected in a flowstream of an appropriate carrier fluid using the zero-dispersion segmented flow approach of this invention, is confined and concentrated within a small volume, corresponding to the NMR observed volume in the detection coil. (The glass flowcell and silica inlet capillary in these two micrographs have been coated with dichlorodimethyl silane to make their surfaces less hydrophilic and more wettable by the carrier liquid).

FIGS. 2A-2D show a comparison of unfavorable, favorable, and ideal conditions for zero-dispersion segmented flow transport of sample plugs. In these micrographs, the sample is DMSO with 10 mg/mL of the blue dye methyl green and the carrier liquid is the colorless fluorocarbon FC-43. FIG. 2A shows that an uncoated fused silica capillary provides unfavorable conditions for these fluids; the DMSO plugs are hour-glass-shaped, showing that the sample wets the bare silica wall preferentially over the fluorocarbon. The smear at the left is from a film of DMSO retained on the capillary wall as the plug was moved into its photographed position. This smear has started to contract into a drop on the wall. PTFE Teflon® (FIG. 2D) provides ideal conditions, as shown by the sausage shape of DMSO plugs in a Teflon® coated capillary, and the tangential contact angle of the FC 43 with the wall indicates the wall is wetted by fluorocarbon even in the presence of a stationary sample plug. As shown in FIGS. 2B and 2C, fused silica capillaries coated with the fluoroalkyl silane perfluorooctyl silane (PFOA) are also preferentially wetted by fluorocarbon; moving DMSO plugs do not leave a film on the wall but can contact the wall if left stationary. All capillaries shown are 200 μm i.d.; the fused silica capillaries are 360 μm o.d., and the Teflon® capillary is 400 μm o.d.

FIG. 7A shows a separation channel 42, which may be, e.g., for carrying out electrophoresis or liquid chromatography. A band of analyte 44 is shown approaching a side-channel 46, which is to be used for sample recovery. The side channel intersects a third channel 48, which has a favorable wall material for carrying out zero-dispersion segmented flow according to the invention and is filled with an immiscible carrier fluid. As shown in FIG. 7B, when analyte band 44 arrives at side-channel 46, it is drawn into valve 50 by the action of syringe pump 47. In FIG. 7C, the withdrawn analyte band 44 is transferred as an immiscible plug to the third channel 48, by movement of valve 50, and transported, via the action of a second syringe pump 49 through the third channel 48 to a collection coil 52, and then to subsequent processing or to a storage capillary.

FIG. 8A is a sectional view through the line AA indicated in FIG. 8B, a plan view of a simple T injector, which is shown as a representative microfluidic analysis chip. The samples are made to flow through the chip and may be recovered. The provided samples may be analyzed in transit, or smaller volumes 66 may be withdrawn from the provided samples, as indicated in FIG. 8B. As sample plugs 64 segmented by carrier fluid 62 flow through the device along the main channel AA, a smaller flow to reservoir b or c causes a smaller segmented flow of a small volume 66 of each sample 64 to migrate towards to the analysis channel bd. In the embodiment illustrated, the samples 64 have been provided to the device from a supply capillary coil, which may have been filled as was the collection capillary coil 52 of FIG. 7C.

DETAILED DESCRIPTION OF THE INVENTION

The purpose of activities leading to the invention was to develop an automated segmented flow NMR method that could increase throughput, could utilize low-mass samples efficiently (with minimal sample loss) and could accept samples from a 96-well plate. The target application was high-throughput NMR analysis of a combinatorial chemistry library. The primary goal of the development activity was to achieve the highest possible throughput that yielded spectra of sufficient quality to be interpretable by automated spectral analysis software. Gains in sensitivity and sample utilization were also desirable to detect, and if possible to identify, contaminants at the 5% level. Sample-to-sample carryover had to be below 1%, the high operating cost of deuterated solvent consumption was to be reduced as much as possible, and the method was to be implementable with commercially available instrumentation. These development activities led to the method of the invention, a zero dispersion method of segmented flow analysis, implemented at the microscale level.

Figure 4A:
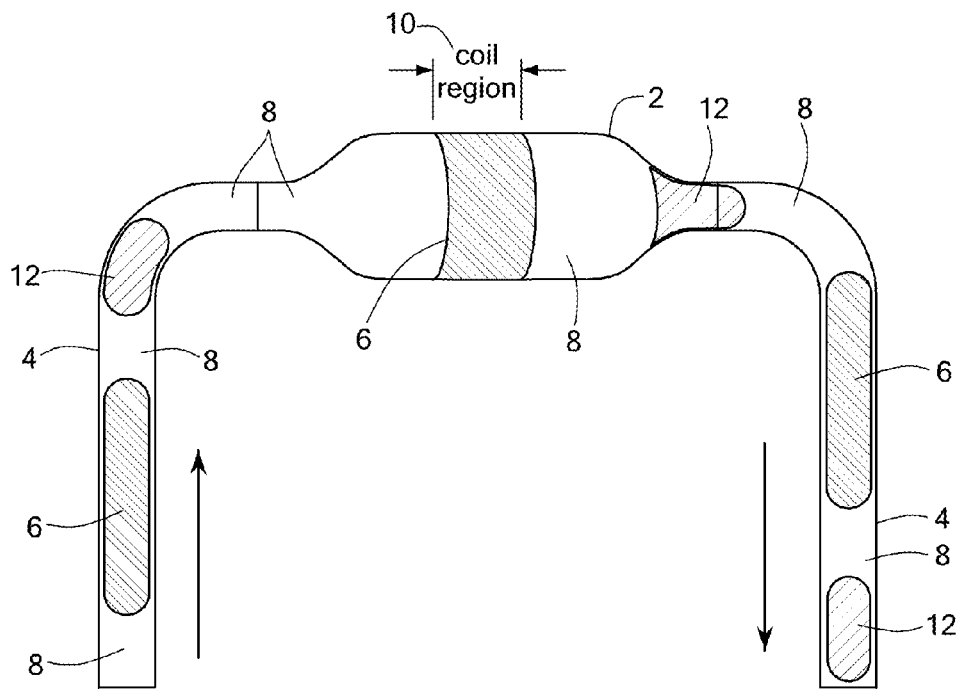
FIG. 4A is a schematic diagram of an implementation of the present invention for high-throughput micro-NMR analysis. Samples 6 (in DMSO), which can be the same or different, were loaded as a queue or train of "plugs" separated and carried by an immiscible liquid 8 (FC 43) towards microcoil NMR flow cell 2. Samples were changed by advancing the queue, as further illustrated in FIG. 5, until the next sample plug was centered in the NMR detection coil region 10. Wash plugs of solvent 12 were included between samples to reduce carryover in non-ideal components. As can be seen in FIG. 4A, at the higher linear velocity in the narrow inlet and outlet capillaries 4, the plugs are separated from the capillary wall by a layer of the carrier liquid. At the slower linear velocity in the wider space of microcoil flow cell 2, the plugs may contact the surface.

As an example, a zero-dispersion segmented flow approach according to the invention, as applied to microcoil NMR analysis (SFA-NMR) is illustrated in FIG. 4A, a schematic diagram of a microcoil NMR flow cell 2 and adjoining capillary tubing 4, which contains several sample plugs 6 separated by an immiscible carrier fluid 8. One sample plug is centered on the NMR detection coil region 10 at the moment flow would be stopped, and a wash plug 12 of clean solvent precedes and follows each sample plug 6. Because samples do not disperse into the immiscible carrier, the sample plug volume may be the minimum required to obtain high-resolution spectra (typically, twice the NMR coil observed volume). Consequently, because samples are not diluted during transfer to the probe, comparable NMR data quality may be obtained with shorter acquisition times than when using an FIA-NMR method. Additionally, because the concentration is uniform over the plug, there is not a 1-2 minute equilibration time after injecting the sample before good lineshape can be obtained. In the segmented flow approach of the invention to high throughput, the entire transfer line to the sample handler can be filled with a queue of many such sample plugs, separated by carrier fluid and by wash plugs (if desired). The detection cell is cleared of the old sample, washed, and filled with new sample in rapid succession by advancing the queue through the distance of one sample-to-sample separation. Successful implementation of SFA-NMR according to the method of the invention requires that sample plugs be moved through several meters of transfer capillary between the sample loader and the NMR probe without the plugs becoming fragmented or analyte adsorbing onto capillary surfaces.

Zero dispersion segmented flow methods (Patton, 1997) have been demonstrated in larger scale systems and are based on the principle that if the carrier fluid has a favorable contact energy with the tubing wall, relative to the sample, a film of carrier is maintained between the wall and the sample as sample plugs are moved through the tubing, or conduit (Patton, 1997; Nord, 1984; Adler, 1973). The combination of a fluorocarbon carrier liquid in Teflon® tubing was recently demonstrated in continuous flow PCR, a method that is particularly sensitive to carryover (Curcio, 2003). The fluorocarbon FC 43 has been used in building microcoil probes to match the magnetic susceptibility of the copper wire of the coil (Olson, 1995) and has been shown to improve line shape when used to "bracket" small aqueous sample plugs in microcoil NMR (Behnia, 1998; Webb, 1996). FC 43 also has a relatively high viscosity (2.8 cs) among fluorocarbons, which favors film formation (Nord, 1984).

However, the performance of segmented flow in microfluidic devices of the prior art tends to be poor. Many preferred conduit materials, such as glass, fused silica capillary, PEEK tubing or fittings, metal and polypropylene sample tubes or microtiter plates, will retain a film of aqueous or organic solvents and are poorly wetted by fluorocarbon liquids. Treatment of glass with dichlorodimethyl silane, a conventional well-known hydrophobic coating, is able to abrogate this permanent film retention and permit plugs to be moved slowly, but does not result in zero dispersion. At the microscale level, in conduits below 200 µM i.d., the sample plugs exert an outward force against the conduit walls, and air bubbles cannot be used to segregate segments because bubbles compress to the point of disappearance at the backpressures encountered.

The key to successful practice of the method of the invention for microscale analysis in microfluidic devices, such as the detection cell of an NMR microcoil (or probe) or other microfluidic device such as a microfluidic chip, which are frequently made of glass, fused silica, silicon or other material not easily wettable by fluorocarbon materials, is to ensure the wettability of the conduit wall by applying to the wall a coating that will change its properties. Treatment of glass or silica surfaces with perfluoroalkylsilanes, using covalent bonding methods (Karger, 2002), can transform silica into a favorable material for zero dispersion segmented flow at the microscale level.

For achieving zero dispersion segmented flow in the transport of samples into and out of a microfluidic device, such as a microcoil NMR flow cell, a flexible material that is inherently preferentially wettable by the carrier liquid is connected to the conduit through the device. Teflon® is a class of exemplary conduit materials to use with a perflourinated liquid carrier fluid, which is immiscible with either aqueous or most organic solvents used for analytical samples. Teflon®, however, has poor mechanical properties for many microfluidic applications: it is difficult to machine or etch channels in, it is resistant to adhesives, castable Teflon®'s are not resistant to fluorocarbon liquids, and Teflon® capillaries have poor pressure resistance and are difficult to connect to other components. Thus, microfluidic devices in practice will include many materials that are inherently unfavorable for segmented flow.

In exemplary embodiments of the method of the invention, the preferred immiscible carrier is a fluorocarbon liquid, which is immiscible with both aqueous and organic solvents (apparently all solvents and analytes other than mixed hydrocarbon-fluorocarbon solvents). The transfer conduit (or tubing) leading into a microfluidic device for practicing the method of the invention preferably is made of a perfluorinated or highly fluorinated material, and the conduit within the device is coated with such a material, so that the conduit inner wall surface is preferentially wetted by the fluorocarbon carrier liquid as compared to the sample solvent. In this case, a film of the fluorocarbon carrier liquid is maintained between the conduit wall and the sample as it passes, such that the sample for analysis does not contact the conduit wall. This prevents adsorption of the analyte to the wall directly or bulk loss of the analyte solution to film formation on the channel wall.

The above features permit efficient transfer of small discrete samples for analysis through conduits leading into, out of and within microfluidic devices, which is a marked advantage for successfully processing samples compared to uniformly filling the channels, to injecting plugs of sample in clean sample solvent as a carrier fluid, or to using an immiscible organic solvent as carrier liquid without such a coating of the conduit wall as in the method of the invention.

The following examples are presented to illustrate the advantages of the present invention and to assist one of ordinary skill in making and using the same. These examples are not intended in any way otherwise to limit the scope of the disclosure.

Materials and Methods

Materials. Polyimide-clad fused-silica capillaries were obtained from Polymicro Technologies (Phoenix, Ariz.), and the fluoroalkyl silanes were purchased from United Chemical Technologies (Philadelphia, Pa.). Fluorocarbon FC 43 was from 3M Corp (St. Paul, Minn.). Teflon® capillaries and tubing were obtained from Cole-Parmer (Vernon Hills, Ill.); PEEK capillary, unions, in-line filters, and adapters were from Upchurch (Oak Harbor, Wash.). The 96-well PCR plates were obtained from Nunc (Rochester, N.Y.). The compounds of the test library (uracil, reserpine, erythromycin, chlorpromazine, tolbutamide, indomethacin, haloperidol, 4-acetamidophenol, indapamide, prilocalne, phenylbutazone, and brucine) were from Sigma. Deuterated solvents and the reference standards tetramethylsilane (TMS) and trimethylsilylproprionate (TMSP) were purchased from Cambridge Isotope Labs (Andover, Mass.). All other solvents, buffer salts, and dyes were obtained from Fisher Scientific (Pittsburgh, Pa.) and were used without further purification.

Instrumentation. NMR spectra were acquired on a Varian (Palo Alto, Calif.) Inova spectrometer with an 11.7-T (500 MHz) actively shielded magnet and a flow NMR package consisting of a Gilson (Middleton, Wis.) model 215 sample handler and Varian VAST automation software. The Gilson 215 was fitted with a 100-µL syringe, and supplemental VAST automation programming (Tcl scripts) was written, as described below. A sample loader, model HTSL-1100, from Protasis Corp (Marlborough, Mass.) consisted of a sample loop valve, high-pressure pump, and microprocessor controller. It could either be triggered to deliver a specified volume and rate, or it could be controlled through an RS232 serial connection.

The microcoil NMR probe principally used was built in-house, as previously described (Kautz, 2001; Olson, 1999). Briefly, referring to FIG. 4A, copper wire (7.5 turns of 50 µm wire) was wrapped on a glass flow cell 2 with 660 µm i.d., 920 µm o.d. The 1.1-mm coil 10 enclosed an observed volume of 0.5 µL of the flow path lumen. The flow cell was ~0.8 cm long, tapering over an additional 1.5 cm on each side to match the inner diameters of 75/360 and 100/360-µm i.d./o.d. fused-silica inlet and outlet capillaries 4. All but 5 cm of the 75-µm inlet capillary was replaced with 100-µm-i.d. Teflon® tubing. The glass and silica elements of the flow path were coated with perfluorooctyl silane (PFOS), as described below. The circuit was singly tuned to a proton frequency of 500 MHz, and spectra were acquired unlocked.

Preliminary data were obtained using a commercial microcoil probe, the $^1$H capLC microflow probe (Olson, 2004) manufactured by Magnetic Resonance Microsensors (MRM, Savoy, Ill.) and distributed by its parent company, Protasis Corp. This probe had a 1.1-µL observed volume ($V_{obs}$) in a flow cell volume of ~3.5 µL, with 50-µm fused-silica inlet and outlet capillaries. When this probe was used, all connections in the sample loop and transfer lines were made using Upchurch PEEK unions.

Figure 5:
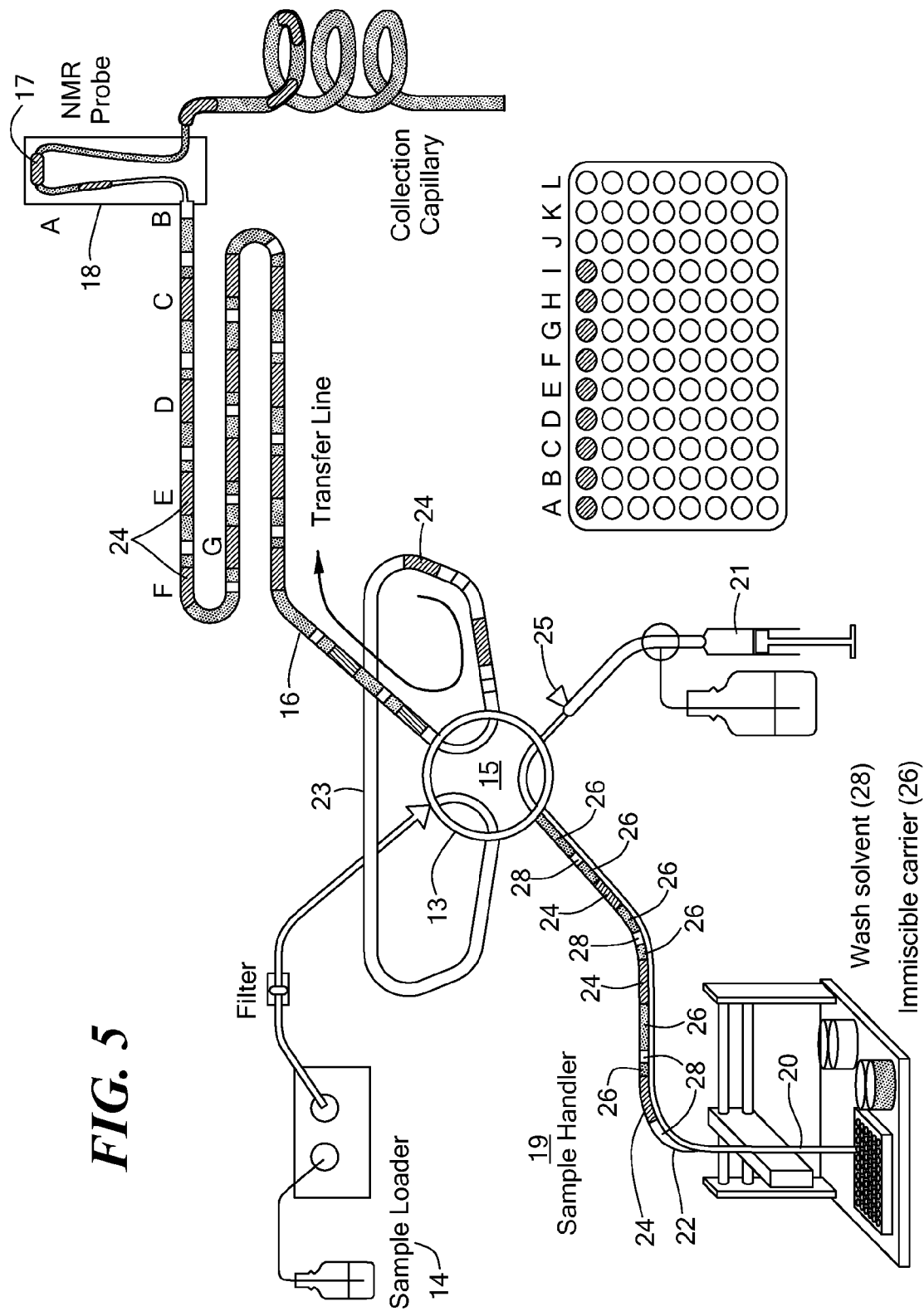
FIG. 5 is a schematic diagram of the system of FIG. 4A incorporated into an apparatus for segmented flow analysis by NMR using the method of the present invention. The depicted apparatus includes sample handler 19; Protasis HTSL-1100 sample loader, which includes pump 14 and sample loop 23 mounted in sample loop valve 13; and transfer line 16 to the NMR probe 18. In the illustrated, or first, position of sample loop valve 13, its rotor 15 is oriented to connect the sample handler needle 20 directly to the sample handler syringe 21 via the lower portion of valve 13 as shown. The sample handler syringe 21 is then operated to form sample plugs and to draw the plugs into needle line 22, a 200-μm-i.d. capillary threaded through sample handler needle 20. The plugs are formed in needle line 22 by alternately drawing samples in DMSO 24, the immiscible fluorocarbon FC 43 26, and intervening wash plugs of solvent 28. Next, rotor 15 is rotated a third of a turn to the second position (not shown) of sample loop valve 13 to connect sample loop 23 in line between the sample handler needle line 22 (within needle 20) and the sample handler syringe 21. The sample handler syringe 21 is then operated to draw the plugs from the needle line 22 completely into sample loop 23 so as to load the sample loop with a train of samples, immiscible carrier fluid and wash plugs. Then, with another third of a turn of rotor 15 (back to the illustrated position), sample loop 23 is connected in line between sample loader pump 14 and transfer line 16 via the upper portion of valve 13 as shown. Operation of pump 14 causes samples 24 to advance in sequence through transfer line 16 to the NMR probe 18. Alternatively, the second position of sample loop valve 13 may be used to load sample handler needle line 22 and sample loop 23 in one step by the operation of sample handler syringe 21, if preferred for a specific application.

The sample handler and loader were connected to the NMR probe as shown in FIG. 5. Both the needle line 22 and sample loop were 70 cm of 200/400-µm i.d./o.d. Teflon® capillary; the transfer line 16 to probe 18 was 2 m of 150/400 Teflon® capillary; the probe inlet consisted of 1 m of 100/400 Teflon® with a residual 5 cm of 75-µm-i.d. fused silica at the connection to the flow cell 17. To connect the soft Teflon® capillary to valves or unions, 2-cm-long pieces of PFOS silica (see below) were butt-jointed to the Teflon® using shrinkwrap tubing. Bleed valve 25 facilitates flushing the sample handler path. The bleed valve 25 was connected to sample handler syringe 21 with 1 m of 500-µm-i.d. 1/16-in-o.d. PEEK tubing, and all remaining connections were made using 250/360-µm i.d./o.d. fused silica. Before each use, the system was flushed with FC 43, freshly degassed under vacuum. Flow rates and system volumes were measured by displacement of a dye plug in a calibrated section of 30-gauge Teflon® tubing (~300 µm i.d.) capturing the effluent from the probe outlet capillary.

PFOS Silica. Probes were internally coated with a tridecafluoro-1,1,2,2-tetrahydrooctyl-1-trichlorosilane (perfluorooctylsilane, PFOS) monolayer. Surfaces were first activated by washing with 1 N NaOH for 1 h, followed by sequential rinses with water, acetone, and chloroform. A fresh 5% (v/v) solution of PFOS in chloroform was flushed slowly through the probe for 1 h, then the probe was rinsed sequentially with chloroform, acetone, and 10% $D_2O$ in acetone. Surfaces were exhaustively dried with an acetone rinse followed by air flow overnight, then the probe was stored filled with FC 43.

Fused-silica capillaries were coated with a thicker PFOS gel layer using the trimethoxy form of PFOS according to the manufacturer's protocol (United Chemical Technologies). In brief, fused-silica capillaries were washed with peroxide/sulfuric acid, then activated with 1 N NaOH overnight. A solution was first prepared of 95% methanol and 5% water, with acetic acid added to an apparent pH meter reading of 5. Subsequently, 4% (v/v) tridecafluoro-1,1,2,2-tetrahydrooctyl-1-trimethoxysilane was added with vigorous stirring and allowed to react for ½ h before introduction to the capillaries for 16 h at room temperature. Capillaries were annealed for 2 h at 80° C., flushed with the methanol/water/acetate solution, blown dry with helium, then cured and dried at 110° C. with helium flow. The capillaries were stored filled with fluorocarbon FC 43 until use.

Automation. Automation was controlled using Varian VAST automation programming on the spectrometer host computer (Sparc Ultra 5, Solaris 8, vnmr 6.1C NMR software). NMR acquisition setup macros were written to (1) automatically detect and position an arriving sample and (2) set up a standard spectrum of a sample (16 scans, 1.05-s acquisition time, 16-Kb points). Referring again to FIG. 5, four sample handler programs (Tcl scripts) were written to (1) form a train of four samples 24 and hold the train in the needle line 22, (2) draw a train from the needle line into the sample loop 23, (3) change samples by triggering the sample loader to run until stopped by the autodetection macro, and (4) initialize the sample queue by moving a sample train one-half of the distance through the transfer line 16 from the sample loop 23 to the NMR probe 18. The sample loader was controlled by means of Unix shell scripts, which could be called from either vnmr macros or tcl scripts.

Sample Preparation. The test library of 12 known pharmaceutical entities was prepared as 1-mL aliquots at 30 mM in DMSO-$d_6$ and stored at 4° C. For carryover measurements, standard samples were 4% chloroform-h in DMSO-$d_6$ (standard S1) and 2% acetone-$h_6$, 5% green food color in DMSO-$d_6$ (standard S2). Ninety-six-well plates were typically alternating columns of S1 and S2, with the third and sixth columns replaced by the 12-member model library. For automated NMR runs, all wells contained 3 µL unless otherwise indicated, and plates were covered with adhesive film. Sample plates were placed on 4-mm foam rubber pads on the sample handler racks, carefully positioned under the needle, and taped into position. Two additional vials on the sample handler rack supplied 0.5 mL of FC 43 and 0.1 mL of the wash/autodetection solution, 1% TMSP (60 mM) in DMSO-$d_6$.

NMR Spectroscopy. Sample spectra shown in FIG. 6 were 16 transients of 16-Kb points, 8000-Hz width, 45° tip angle, auto gain, with no additional relaxation beyond the 1.05-s acquisition time. The spectra were processed by zero-filling to 64-Kb points and Fourier transformed with 1 Hz of exponential line broadening. (Line widths are reported with no line broadening.) Autodetection used single scan spectra with a 60° tip angle, fixed gain, and other parameters as above; the region from −0.5 to +0.5 ppm was monitored for a peak with S/N>10 to detect the TMSP in the wash plugs. The COSY spectrum was a magnitude COSY, 128 increments of transients processed with linear prediction in t1 to 512 points, apodized with sinebell-squared matched to acquisition time in both time domains. Total acquisition time was 10 min.

Example I

Feasibility Studies and Method Development

Preliminary studies were made, observing the movement of DMSO sample plugs using FC 43 as the carrier fluid in capillaries of several different materials. In the Teflon® capillary, FC 43 was the continuous phase: DMSO plugs did not contact the capillary wall and could be moved through several meters with no detectable carryover (<0.1%) or losses at all flow rates tested (0-20 µL/min). In the plain fused-silica capillary, DMSO was the continuous phase, retention of a DMSO film depleted sample plugs by 2 µL for each meter of movement (in 200-µm capillary). In the PFOS-coated silica capillary, neither phase was continuous: a DMSO film was not retained, so sample losses were negligible at modest flow rates (1-10 L/min); however, carryover of minute droplets could occur (10-100 nL/m) if imperfections existed in the coating. It was also found necessary to push the sample train through the NMR probe under positive pressure rather than to pull samples through the system with a syringe or peristaltic pump at the detector outlet, as in a traditional SFA system (Patton, 1997). The flow rate of FC 43 through the microcoil probe with vacuum applied to the outlet capillary was <1 µL/min; changing samples in 30 s would require a flow rate on the order of 10 µL/min, which could be obtained with modest pressures of 150 psi. Therefore, a strategy of pulling sample and FC 43 plugs into a sample loop and then pushing the sample train through the transfer line and microcoil NMR probe by positive displacement was pursued.

To facilitate adoption of the method, it was implemented by modifying a conventional microVAST installation. The sample handler and loader were connected with the microcoil NMR probe using Teflon® capillary tubing, as shown in FIG. 5. Sample plugs 24 were loaded into the sample loop 23 by drawing consecutive plugs of FC 43, wash solution, FC 43, and sample via a 200-µm Teflon® capillary line 22 threaded through the sample handler needle 20. The transfer line 16 to the NMR coil 17 of NMR probe 18 held two trains of four samples with a 7-µL gap between them. The transfer line to the probe was 3 m long with a dead volume of 43 µL; the total dead volume from needle tip to NMR observed volume was 92 µL.

Samples were automatically positioned in the NMR coil by calibrating a delay between initial detection of their NMR signal (FC 43 has negligible 1H or 2H signal) and stopping the sample loader. The sample handler 19 could operate independently of the NMR spectrometer and sample loader 14 through the use of sample pump syringe 21; for example, during the time sample loop 23 was slowly clearing and as four NMR spectra were being acquired from the samples in the train in the NMR probe 18 (with samples being advanced (changed) by the sample loader 14 after each spectrum acquisition), sample handler 19 was being used to form a new sample train from the next four wells of the microtiter plate. To avoid interrupting analysis, this new train was held in the needle line 22 until the sample loop 23 was cleared. Operation of pump 14 was stopped when each sample 24 was resident in the NMR observed volume (coil 17) to permit NMR data acquisition, which may require only a few seconds or be as long as several days or longer. Movement of the pump 14 was resumed after NMR data acquisition, until the next sample 24 was positioned in the NMR probe 18.

Once assembled, the system was calibrated, and flow rates, plug volumes, and automation timing were optimized. A flow rate of 7 µL/min did not overpressure the 200/400-µm i.d./o.d. Teflon® capillary sample loop. Plugs of FC 43 as small as 0.3 µL were equally as effective as larger plugs in separating DMSO plugs through the probe, as measured by carryover. Plugs of FC 43 of 0.7 µL or larger provided several seconds with no NMR signal during on-flow NMR, which facilitated autodetection. In calibrating the positioning delay after automatic detection, it was found that variability in signal strength among samples caused variation in positioning, so 1% TMSP was added to the wash plugs to provide a consistent signal for detection. The variability of automatic sample plug positioning was (0.2 µL, due primarily to the 1-s intervals used for initial detection. The 2 µL sample plugs provided NMR line widths below 1.5 Hz without reshimming over a 0.5 µL window, and no equilibration time was required after stopping flow to observe good line shape. For manual injections, sample plugs of 1 µL could be shimmed to routine probe specification of 1.2 Hz. When samples were drawn directly into segmented plugs, 2.0 µL of 2.5 µL deposited into the individual wells of 96-well plates was able to be recovered. Manual recovery of 2.0 µL from a PFOS-coated vial using PFOS-silica capillary was also possible. The ability to accurately position samples within the detection volume based on the distinct leading edge was another significant advantage over FIA methods, where the optimum position was easily missed.

Example II

Performance of the Automated SFA-NMR System

The performance of the automated system was evaluated by loading samples and acquiring spectra from 96-well plates with 3 µL/well of test library compounds (30 mM in DMSO-$d_6$) interspersed with standards for assessing carryover and line shape. Automated analysis completed in 2.5 hr/plate, plus 24 min to initialize the queue in which four trains were drawn and two were injected. This initialization time is reported separately because it applied to the first plate but not to subsequent plates of continuous high-throughput operation. Spectra were output at rates of 1/min along each train of four samples. The sample change and wash was completed in 35 s, NMR acquisition was set to 16 s, and the automation software required 10 s of execution and dead time. Sustainable throughput was 1.5 min/sample due to the time required to draw a new train from the needle line into the sample loop and to advance the queue through the gap between trains (105 s).

Figure 6:
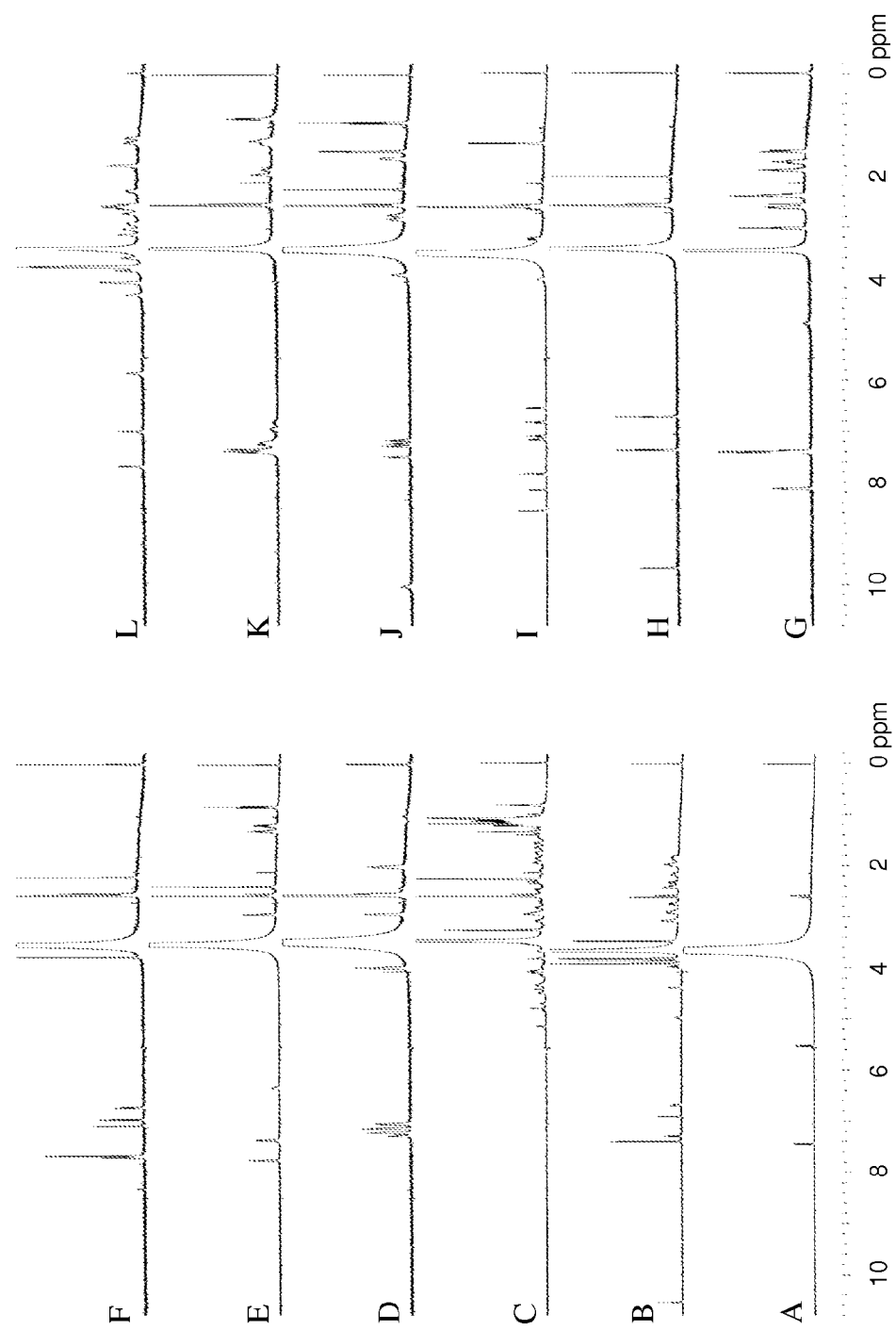
FIG. 6 shows NMR spectra of a model compound library acquired using segmented flow analysis NMR according to the invention. The average throughput was 1.5 min/spectrum, using 2 μL of 30 mM analyte. Each spectrum was the sum of 16 1-s transients. Compounds: uracil (A), reserpine (B), erythromycin (C), chlorpromazine (D), tolbutamide (E), indomethacin (F), haloperidol (G), 4-acetamidophenol (H), indapamide (I), prilocalne (J), phenylbutazone (K), and brucine (L).
Figure 7A:
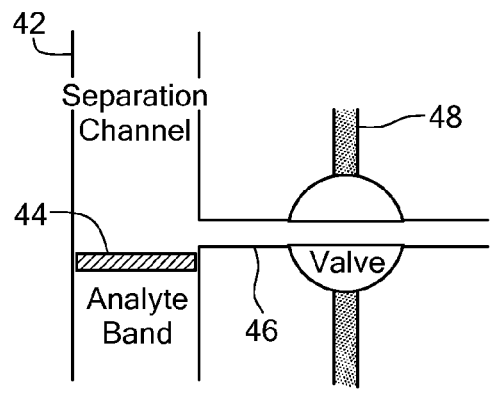
FIGS. 7A-C show an embodiment where the invention is used for collecting and transporting samples of materials purified and isolated by microseparations.
Figure 7B:
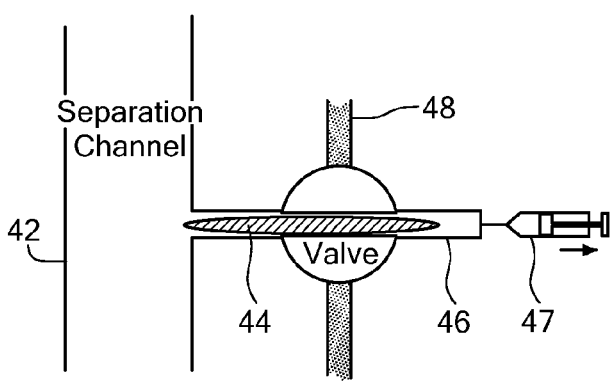
Figure 7C:
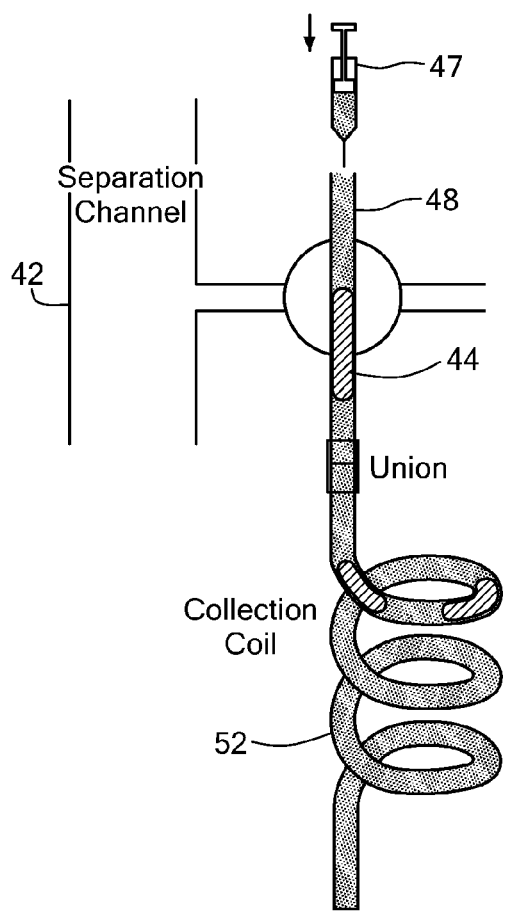
Figure 8A:
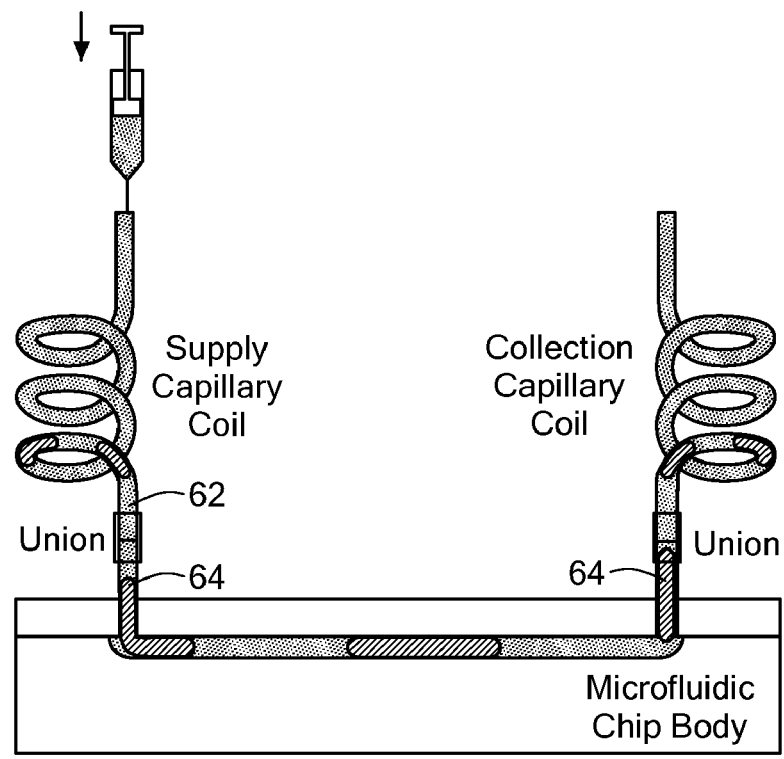
FIGS. 8A-B show a "world-to-chip" interface, whereby laboratory frame samples may be readily applied to, processed in, and recovered from a microfluidic chip according to the method of the invention.
Figure 8B:
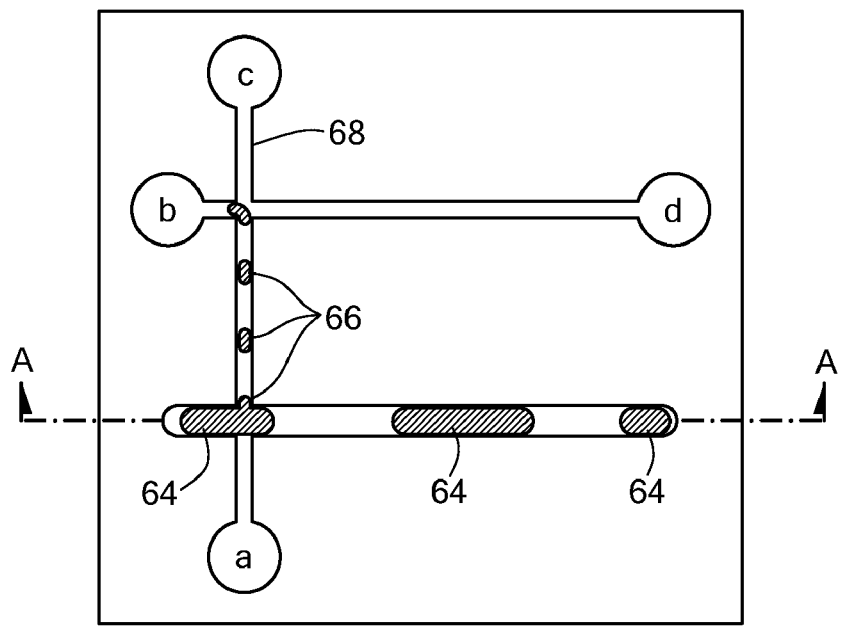
Figure 9:
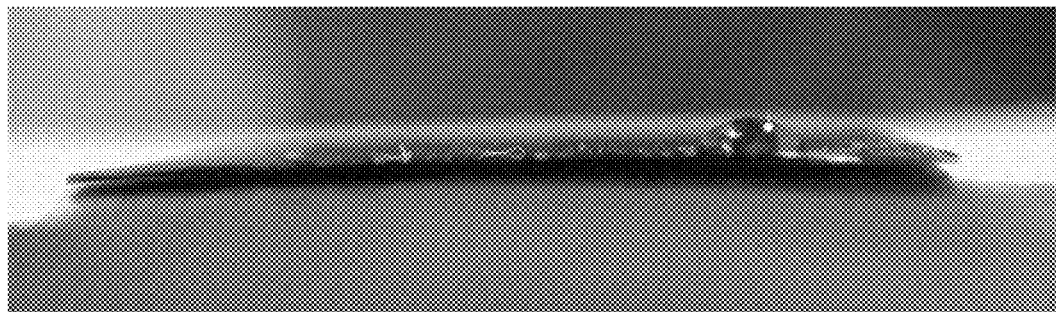
FIG. 9 is a micrograph of two water droplets on a 3 cm wide silicon wafer. The right side of the wafer has been coated with perfluorooctyl silane; the left side has merely been cleaned with lye. A 10 μL droplet of water was applied to each side, and smeared over 1 $cm^2$. The water is repelled by the PFOStreated silicon, so it re-forms a sitting drop with a contact angle of nearly 90 degrees. The untreated silicon is wetted, and the resulting water film is not apparent in the micrograph.

Spectra of the 12 test library compounds are presented in FIG. 6. The sensitivity of all spectra was sufficient to unambiguously confirm the structures of the compounds. The weakest signals of these 12 compounds were the multiplet at 5 ppm in reserpine (spectrum A) and the 18-Hz-wide amide of tolbutamide at 6.2 ppm in FIG. 6E, both with S/N=15. The intensity of most signals was within the range of 130 and 23. Thus, even with the moderate sensitivity of this home-built probe, it should be possible to identify compounds at 3-fold lower concentration (10 mM) or to detect impurities at the 5% level. For example, minor resonances visible in spectrum K (phenylbutazone) at 6.8 ppm were 13% of the net aromatic intensity.

Compound identification may at times require advanced 2D spectra, or it may be desirable to analyze samples in protonated solvents requiring solvent suppression. Consequently, care was taken in programming the method so that existing macros for setting up established methods could be inserted, such as for gradient shimming, scout-scan solvent suppression, or 2D spectra. For example, a macro to acquire a magnitude COSY spectrum was added as a single line to one automation queue as described in Kautz, 2001. This flexibility was made a priority in development in order to enable 2D spectra to be acquired in a data-dependent manner, that is, to acquire a COSY or TOCSY spectrum if automated analysis of a 1D spectrum fails to confirm an expected product.

Importantly, the analyte in immiscible sample plugs was not found to disperse with time, so extended stopped flow acquisitions were possible without loss of signal strength due to dilution of the sample in the NMR coil. For example, in a 72-h acquisition of a trace sample (data not shown), the first 8-h block of data acquisition was identical to the last 8-h block. This stability also made it possible to interrupt long high-throughput analyses. One automation run of a 96-well plate was suspended in software, and the microcoil probe was removed from the magnet without disconnecting the transfer line. After the spectrometer had been used with a different probe for several hours, the microcoil probe was reinstalled, the automation queue was restarted, and analysis of the plate completed without any problems. Sample plugs in Teflon® tubing have been stored for over 1 yr refrigerated without degradation of the plug nor the analyte.

Sample carryover was below 1%, determined by comparing integrals of solvent peaks between alternating samples of 2% acetone and 4% chloroform, with one wash plug between them. A dye test showed that carryover to the wash plugs in the inlet capillary was in the range of 20-30 nL (<1%), suggesting most of the 5% sample-to-wash plug carryover observed at the NMR coil occurred in the residual 75-μm fused-silica segment of the inlet. The line widths obtained when automatically positioning sample plugs, evaluated from single-scan spectra, were between 1.0 and 1.6 Hz, close to the routine line width obtained with this probe (1.2 Hz). Importantly, the cost of deuterated solvent consumption was negligible: 0.4 mL of DMSO-$d_6$/plate at $2/mL, including 100 μL of DMSO-$d_6$ supplied as wash solvent in addition to the 96 3-μL samples.

The efficiency of sample utilization of the method of the invention for NMR analysis (SFA-NMR) was comparable to that attained using capillary isotachophoresis (cITP) (Kautz, 2001; Wolters, 2002b), the most sensitive applied NMR method to date. Moreover, SFA-NMR can be used to relatively quickly load analytes with unknown or zero electrophoretic mobility, which is important for de novo analysis of trace amounts of isolated natural products or drug metabolites. However, most separation and concentration methods cannot be put into practice in situ in the remote confined location of the magnet bore. SFA-NMR permits microseparations and microconcentration to be performed using optimal bench top techniques and instrumentation as long as a 1-μL fraction can be collected for subsequent transfer to the NMR microcoil.

SFA-NMR, as demonstrated above, doubled the throughput, quadrupled the sample efficiency, and reduced deuterated solvent consumption over 20-fold as compared to the commercially supported high-throughput flow NMR methods. Nonetheless, a number of straightforward improvements may still be envisioned. For example, lengthening the transfer line to hold 3 trains without gaps would increase throughput by eliminating the longer sample change time between trains. A larger i.d. sample loop could double the rate of loading the sample loop and could hold more samples in longer trains. Using a 10-port sample loop valve to switch between two loops would eliminate the delay to draw new trains into the sample loop. These and other improvements would increase the throughput of SFA-NMR to over one 96-well plate/h. Using segmented flow to alternately load multiple flow cells (Macnaughtan, 2003; Wolters, 2002c) could additionally increase throughput, reaching essentially continuous NMR data acquisition.

ADVANTAGES AND OTHER EMBODIMENTS

Because sample efficiency is high and no sample is wasted using the method of the invention, trace samples may be analyzed. In fact, use of sample may be 100% efficient, as opposed to 10-30% (in commercial Protasis/MRM microinjection) or 0.1% (filling a 200 μm microcoil probe). There is no degradation of sensitivity or resolution if sample plugs as small as 1 μL are picked up by the autosampler and transferred into an NMR probe with a 3.5 μL flowcell/1 μL observe volume.

Rapid sample changes are possible along a queue of sample plugs. Conventionally, a sample loaded in the sample loop must be delivered the entire distance to the NMR coil. With the immiscible plug method according to the invention, small sample plugs may be closely spaced, separated by plugs of the immiscible solvent (segmented flow injection). For example, if 1 μL sample plugs are separated by 0.5 μL of immiscible liquids, samples may be changed by moving the queue only 1.5 μL.

Rapid washing of an NMR detection cell is possible. In conventional DI-NMR and FIA-NMR methods, the flow cell must be flushed with several volumes of clean solvent between samples to reduce sample carryover. With the method of the present invention, one sample plug may be followed closely with one or more small plugs of clean solvent to rinse any traces of sample from surfaces or dead volumes of the plumbing. This "train" of sample and rinse plugs may be less than 2 μL, and subsequent samples may follow immediately, in a flow-through injection scheme.

No relaxation time is required after sample injection before NMR analysis can be carried out. Because the sample plug is of uniform concentration, there are not strong concentration gradients within the sample as in the conventional methods. The linewidth of the NMR spectrum is sharp immediately upon arrival of the sample in the NMR coil.

Figure 4B:
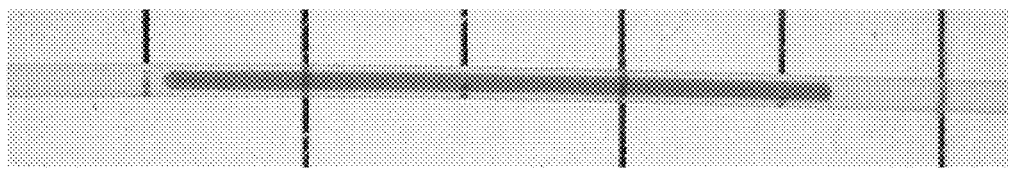
FIG. 4B is a micrograph (with marks every 0.5 cm) of a sample plug (dyed DMSO) recovered after automated withdrawal from a vial, delivery through a 2 meter transfer line, and passage through a commercial microcoil NMR probe, which included 2 meters of 50 micron fused silica capillary in addition to the volume of the NMR flow cell.

Because samples are maintained in their original volume of 1-2 μL, sample recovery is greatly facilitated. The photograph shown in FIG. 4B is, in fact, of a sample plug after passage through a microcoil NMR probe. With a miscible carrier liquid, analytes disperse over a volume of 5-20 μL. Consequently and in addition, the leading and trailing edges of the resulting analyte zone are not well-defined and are difficult to detect. With immiscible solvent plugs according to the method of the invention, the sample zone is sharply defined and can be detected by the physical properties of either the solvent or of the sample itself, or of the sharp boundary, such as UV or visible absorbance, conductance, viscosity, light scattering, surface tension, or others. A conventional liquid chromatography fraction collector may be used. Alternatively, simply placing a length of Teflon® tubing on the outlet capillary of the NMR probe collects the sample and wash plugs, which may be discerned by eye.

Figure 1A:
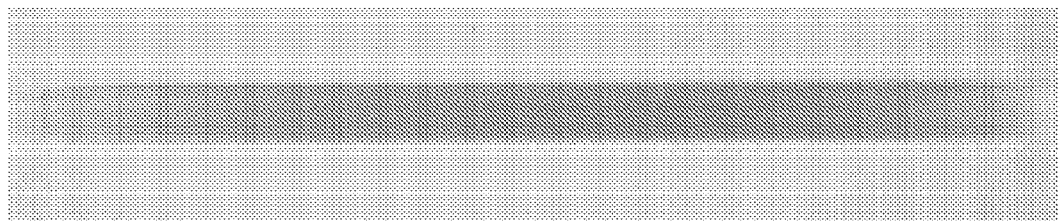
FIGS. 1A and 1B show the efficacy of the present invention through several micrographs of the delivery of a visible dye sample into a glass flow cell under various conditions. The test flow cell is identical in material composition to the microcoil NMR probe flow cell of the microcoil NMR probe used herein, and sample was delivered through 1 meter of 50 micron fused silica capillary.
Figure 1B:
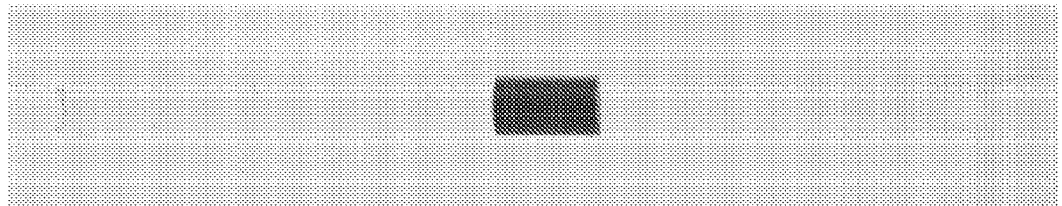
Figure 3:
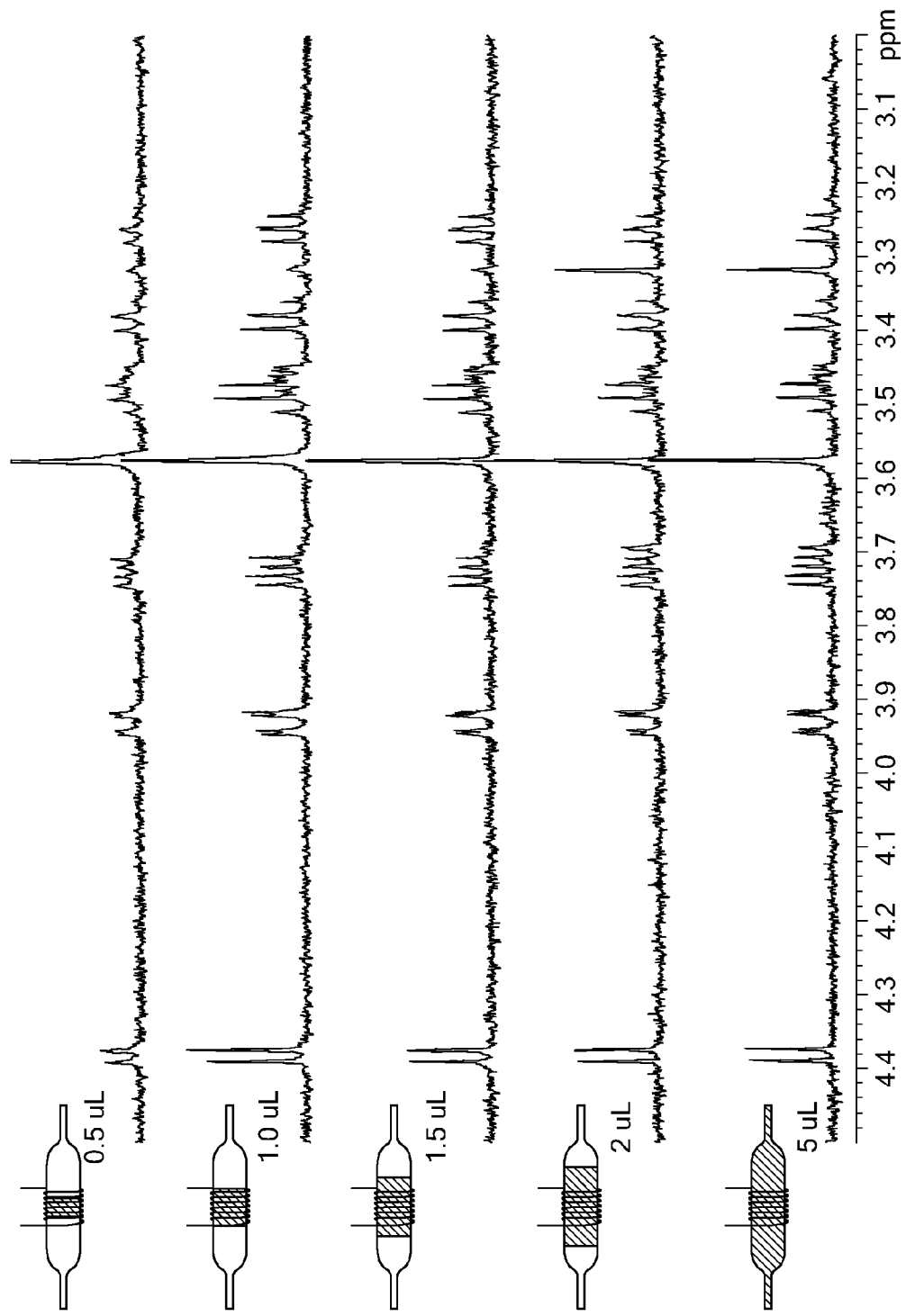
FIG. 3 shows NMR spectra as a demonstration of the improvement in the sensitivity of NMR analysis using the present invention. Five spectra are given, which were acquired from loading of the indicated volumes of a standard sample, 0.3 mg/mL beta-methyl-glucoside in $D_2O$. In the bottom spectrum, the entire NMR flow cell was completely and uniformly filled with the sample (5 μL), in a similar manner to the practice of the conventional direct-injection method. Moving towards the top spectrum, it can be seen that as the volume of the injected sample plug is decreased from 5 μL down to 1 μL, there is no decrease in NMR sensitivity, indicating that the smaller samples are not being diluted by the carrier fluid and still fill the observed volume for detection (1 μL, between the indicator lines). Only when the sample plug is 0.5 μL, or half the size of the NMR observed volume (top spectrum), is there a decrease in signal strength, because only half as many analyte molecules are being detected. The ability to acquire the same quality of spectrum with a sample volume of 1 μL where the conventional art requires 5 μL permits mass limited samples to be loaded at five times the concentration, increasing sensitivity in practice by a factor of five. Cryogenically-cooled NMR probes, which offer a factor of four sensitivity enhancement at a cost of approximately $200,000, are a commercially viable product at the present time.

The diffuse leading and trailing edges of sample plugs in the conventional methods make it difficult to determine the optimal positioning of the sample in the NMR cell. However, with the method of the invention (as shown in FIG. 1B), the leading edge of the sample plug is sharp and easily detected; the plug can be accurately positioned by timing from the arrival of the leading edge.

Samples may be transferred in larger bore capillary tubing, reducing backpressure and consequent need for specialized pumps and related plumbing equipment. Additionally, samples may be transferred over longer distances without loss. High-end NMR spectrometers have larger magnets with larger fringe fields, which may require the sample handler to be as far away as 10 meters. With the present invention, there is no disadvantage in sample efficiency or throughput with longer transfer line lengths. Larger capillaries permit fast transfers even over such distances, where 50 micron capillaries would be prohibitive.

While basic "One-Dimensional" NMR spectra are generally acquired from concentrated samples in a few minutes or less, more information or more dilute samples can require NMR acquisition times of several days or more. Using conventional methods, miscible sample plugs can diffuse out of the detection volume over such long periods of time. However, using the method of the invention, the immiscible sample plugs are stable indefinitely. Plugs stored in Teflon® tubing have remained intact and undiluted for over a year.

Efficient sample transfer by the immiscible plug method according to the invention depends on the relative contact energies of the sample solvent and immiscible carrier solvent with the channel wall. These contact energies can be modified by chemically modifying the channel wall. FIGS. 2A-2D show sample plugs of DMSO-d6 (with blue dye) separated by a fluorocarbon liquid (clear), in Teflon®, fused silica, and perfluoroalkyl silane-treated fused silica capillaries (FAS-silica). The fused silica capillaries are mechanically more rigid, more suitable for higher pressures, and easier to make high-pressure connections. FAS-silica would enable the existing commercial microcoil probes to use the immiscible plug injection method, because the silica can tolerate the back-pressures generated when driving flow through their 50-micron capillaries.

The use of smaller microcoil probes is enabled using the method of the invention. The current (and only) commercial microcoil NMR probe has an NMR coil detection volume ("active volume," "observe volume," $V_{obs}$) of 1 µl, designed based on the typical size of a capillary LC peak, or of the smallest sample that can be injected using a commercial autosampler, considering the limitations of dilution during transfer. With the present invention, samples of arbitrarily small volume may be efficiently transferred into smaller microcoil probes. In particular, the most sensitive microcoil NMR probes produced to date are wrapped directly on 200/360 µm (i.d/o.d.) capillaries and have an observe volume of 30 nL, but sample transfer into the coils is difficult (Kautz, 2001). Using the method of the invention, samples of approximately 30 nL volumes can be efficiently transferred, making these smaller probes, which are three times more sensitive, feasible for routine samples or high-throughput use.

The above work was performed using fluorocarbon FC-43 as the immiscible carrier liquid. Many other immiscible solvent systems, including other fluorocarbon liquids, are available which may be advantageous for their viscosity, immiscibility with unusual analytes or sample solvents, or to match magnetic susceptibility to a particular sample.

Interfacing to capillary separation or concentration microdevices is easy to carry out using the method and system of the invention. A variety of means have been proposed for microanalysis of trace samples by performing separation and concentration of sub-microliter volumes. Most of these systems are practical or viable in an openly accessible system on the benchtop, or within a specialized device. Most cannot be adapted to practice in the confined and inaccessible volume of an NMR magnet bore, and so cannot be used in situ for microcoil NMR as we demonstrated for capillary isotachophoresis. Nor has it previously been feasible to transfer the sub-microliter sample fractions produced by these methods into microcoil NMR probes. The immiscible solvent plug injection method of the invention makes these procedures practical.

Traditional and present methods of flow NMR draw samples from microtiter plates such as 96-well plates with 200 µL wells. Arrays of smaller wells such as 384 well plates or 1536-well plates are also in use. A problem in automated sample handling is positioning a needle into the fluid sample volume and withdrawing a small sample completely without drawing any air. With small samples, a significant fraction of small samples must be left in the well, where it is wasted. By the present method, rather than capturing and storing samples in the wells of microtiter plates, samples could be collected at the source of concentration or separation as immiscible plugs in a length of inexpensive Teflon® tubing filled with the immiscible carrier. The Teflon® tubing may be easily stored and/or transported to a different laboratory for microcoil NMR analysis or other microfluidic analytical methods.

The present invention also enables a more efficient method of handling small samples in conventional microtiter plates. To draw the entire prepared sample into an autosampler needle without drawing air, an immiscible fluid which is lighter (lower density) than the sample solvent may be added to the sample well together with the prepared sample. This lighter immiscible will float on top of the prepared sample. When the sample is drawn into the needle of the sample handling robot, any excess volume drawn will be the immiscible overlay rather than air, and the sample may be efficiently transferred into the microcoil NMR or other microfluidic device.

REFERENCES

Adler, H. et al., 1973 "Continuous Extraction of Body Fluid Samples, Including Whole Blood, Plasma and Urine" in *Advances in Automated Analysis*, Technicon International Congress, Vol. IX; Mediad Inc., Tarrytown, N.Y., 1973, pp. 81-85.

Behnia, B. and A. G. Webb, 1998 "Limited-Sample NMR Using Solenoidal Microcoils, Perfluorocarbon Plugs, and Capillary Spinning". Analytical Chemistry., vol. 70, No. 24, 5326-5331

Curcio, M and J. Roeraade, 2003 "Continuous segmented-flow polymerase chain reaction for high-throughput miniaturized DNA amplification", Analytical Chemistry, vol. 75, pp. 1-7.

Eldridge, G. R. et al. 2002; "High-throughput method for the production and analysis of large natural product libraries for drug discovery" Anal. Chem. 2002, 74, 3963-3971.

Karger, B. L. and Goetzinger, W., 2002, U.S. Pat. No. 6,372,353 "Coated surface comprising a polyvinyl alcohol (PVA) based covalently bonded stable hydrophilic coating"

Kautz, R. A. et al. 2001 "Sample Concentration and Separation for Nanoliter-Volume NMR Spectroscopy Using Capillary Isotachophoresis" J. Am. Chem. Soc. 2001, 123, 3159-3160.

Keifer, P. A., 2003a, "Flow NMR Applications in Combinatorial Chemistry", Current Opinion in Chemical Biology, vol. 7, No. 3, pp. 388-394, June 2003.

Keifer, P. A., 2003b, "Flow Injection Analysis NMR (FIA-NMR): A Novel Flow NMR Technique That Complements LC-NMR and Direct Injection NMR (DI-NMR)". Magnetic Resonance in Chemistry, vol. 41, No. 7, pp. 509-516, 2003.

Keifer, P. A., et al., 2000 "Direct-injection NMR (DI-NMR): A Flow NMR Technique for the Analysis of Combinatorial Chemistry Libraries". Journal of Combinatorial Chemistry, vol. 2, No. 2, pp. 151-171, 2000.

Lacey, M. E. et al., 2001 "1H NMR characterization of the product from single solid-phase resin beads using capillary NMR flow probes", Journal of Magnetic Resonance, vol. 153, No. 2, pp. 215-222, 2001.

Macnaughtan, M. A. et al., 2003 "High-Throughput Nuclear Magnetic Resonance Analysis Using a Multiple Coil Flow Probe", Analytical Chemistry, vol. 75, No. 19, 2003.

Nord, L. and B. Karlberg, 1984 "Extraction Based on the Flow-Injection Principle. Part 6. Film Formation and Dispersion in Liquid-Liquid Segmented Flow Extraction Systems", Analytica Chimica Acta, vol. 164, pp. 233-249, 1984.

Olson D. L. et al., 2004 "Microflow NMR: Concepts and Capabilities", Analytical Chemistry., vol. 76, No. 10, pp. 2966-2974, May 15, 2004.

Olson, D. L. et al., 1999 "Nanoliter-volume 1H NMR detection using periodic stopped-flow capillary electrophoresis" Anal. Chem. 1999, 71, 3070-3076.

Olson, D. L. et al., 1995. "High-resolution microcoil 1H-NMR for mass-limited, nanoliter-volume samples". Science, vol. 270, No. 5244. pp. 1967-70

Patton, C. J. and A. P. Wade, 1997 "Continuous Flow Analyzers", pp 153-155 in Analytical Instrumentation Handbook, 2'nd ed. rev., G. W. Ewing, ed., Marcel Dekker, New York, 1997, Ramsey, J. M. et al., 2003, U.S. Pat. No. 6,524,456 "Microfluidic Devices for the Controlled Manipulation of Small Volumes."

Smythe, W. J. et al, 1969: U.S. Pat. No. 3,479,141 "Transport system for automatic analysis"

Webb, A. G., et al. 1996 "Signal-to-noise and magnetic susceptibility trade-offs in solenoidal microcoils for NMR" J. Magn. Reson., Ser. B 1996, 113, 83-87.

Wolters, A. M et al., 2002a "Microscale NMR" Curr. Opin. Chem. Biol. 6, 711-716.

Wolters, A. M et al., 2002b "Capillary isotachophoresis/NMR: extension to trace impurity analysis and improved instrumental coupling" Anal. Chem. 2002, 74, 2306-2313.

Wolters, A. M., et al. 2002c "NMR detection with multiple solenoidal microcoils for continuous-flow capillary electrophoresis" Anal. Chem. 2002, 74, 5550-5555.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method of moving small samples of liquid through a microscale conduit system, said method comprising carrying out the following steps in the order given:
  a) providing a microscale conduit system, said conduit system having an interior wall surface;
  b) providing a first liquid sample to be transported through said system, said first liquid sample comprising a first solvent;
  c) providing a carrier liquid that is immiscible with said first solvent of said first liquid sample, wherein said interior wall surface of said conduit system, said carrier liquid and said first solvent are selected so that said interior wall surface is wettable by said carrier liquid preferentially to said first solvent and wherein said interior wall surface of at least a first section of said system is provided by a preferentially wettable covalent coating over a conduit system material that inherently, without said preferentially wettable covalent coating, is not preferentially wettable by said carrier liquid;
  d) transferring a portion of said carrier liquid into said conduit system;
  e) causing said carrier liquid to move in said conduit system by transferring an aliquot of said first sample into said conduit system;
  f) causing said aliquot of said first liquid sample to move in said conduit system by transferring into said conduit system a second portion of said carrier liquid; and
  g) causing said first liquid sample and said carrier liquid to continue to move in said conduit system.

2. The method of claim 1, wherein, further, the interior wall surface of at least a second section of said conduit system is provided by a material that, inherently, without a coating, is preferentially wettable by said carrier liquid.

3. The method of claim 1, wherein said microscale conduit system comprises a conduit portion through a microfluidic device.

4. The method of claim 3, further comprising the step of carrying out an analysis or processing step appropriate to said microfluidic device on said first sample when said aliquot of said first sample has been moved into a position in said device appropriate for said analysis or processing step.

5. The method of claim 1, wherein said carrier liquid is a perfluorocarbon.

6. The method of claim 1, wherein said interior wall surface of said first section of said conduit system is made of glass or fused silica, wherein said covalent coating applied to said interior wall surface of said first section is a fluoroalkyl silane and wherein said carrier liquid is a fluorocarbon.

7. The method of claim 6, wherein said fluoroalkyl silane is tridecafluoro-1,1,2,2-tetrahydrooctyl-1-trichlorosilane (perfluorooctylsilane, PFOS).

8. The method of claim 1, wherein said covalent coating applied to said interior wall surface of said first section is an alkyl silane.

9. The method of claim 1, wherein said carrier liquid is a fluorocarbon and wherein said covalent coating applied to said interior wall surface of said first section is fluorine-rich.

10. The method of claim 2, wherein said interior wall surface of said second section of said conduit system comprises polytetrafluoroethylene and wherein said carrier liquid is a fluorocarbon.

11. The method of claim 1, wherein said liquids are caused to move intermittently in said conduit system.

12. The method of claim 1, wherein said liquids are caused to move continuously in said conduit system.

13. The method of claim 4, wherein said processing step is carried out under stopped flow conditions.

14. The method of claim 3, wherein said microfluidic device is a probe for an NMR spectrometer and wherein said conduit portion through said device includes the observed volume of the detection cell for said NMR probe.

15. The method of claim 1, said method further comprising, following step (f) and before step (g), the steps of;
   (f1) providing a second liquid sample to be transported through said system, wherein said solvent of said second liquid sample is also immiscible with said carrier liquid;
   (f2) transferring an aliquot of said second liquid sample into said conduit system; and
   (f3) causing said aliquot of said second liquid sample to move in said conduit system by transferring into said conduit system another portion of said carrier liquid, wherein said steps f1-f3 may be repeated for further said samples.

16. The method of claim 15, wherein said second liquid sample comprises the same solvent as said first liquid sample.

17. The method of claim 15, said method further comprising, prior to step f2, the steps of transferring a portion of a wash solvent compatible with said first solvent into said conduit system followed by transferring a portion of said carrier liquid into said conduit system.

18. The method of claim 4, said method further comprising, following step (f) and before step (g), the steps of;
   (f1) providing a second liquid sample to be transported through said system, wherein said solvent of said second liquid sample is also immiscible with said carrier liquid;
   (f2) transferring an aliquot of said second sample into said conduit system; and
   (f3) causing said aliquot of said second liquid sample to move in said conduit system by transferring into said conduit system a portion of said carrier liquid; and
   following step (g), the step of:
   (g1) carrying out said processing step on said second sample when said aliquot of said second sample has been moved into a position in said device appropriate for said processing step, wherein said steps f1-f3 and step g1 may be repeated for further said samples.

19. The method of claim 17, wherein said second liquid sample comprises the same solvent as said first liquid sample.

20. The method of claim 1, wherein said aliquot of said first sample is overlaid with carrier fluid prior to transfer into said conduit system.

* * * * *